United States Patent [19]

Nelson

[11] 4,139,564
[45] Feb. 13, 1979

[54] 2-DECARBOXY-2-HYDROXYMETHYL)-16-FLUORO-PGE$_2$ COMPOUNDS

[75] Inventor: Norman A. Nelson, Galesburg, Mich.

[73] Assignee: The Upjohn Company, Kalamazoo, Mich.

[21] Appl. No.: 786,153

[22] Filed: Apr. 6, 1977

Related U.S. Application Data

[62] Division of Ser. No. 647,369, Jan. 8, 1976, Pat. No. 4,032,576.

[51] Int. Cl.$^2$ ............................................. C07C 177/00
[52] U.S. Cl. ................................................. 260/586 R
[58] Field of Search ..................................... 260/586 R

[56] References Cited

U.S. PATENT DOCUMENTS

| | | | |
|---|---|---|---|
| 3,914,282 | 10/1975 | Pike | 560/121 |
| 3,932,463 | 1/1976 | Schaub et al. | 560/121 |
| 3,933,889 | 1/1976 | Magerlein | 560/121 |
| 3,959,346 | 5/1976 | Schneidner | 560/121 |
| 3,962,293 | 6/1976 | Magerlein | 560/121 |

OTHER PUBLICATIONS

Burger, "Medicinal Chemistry" pp. 81–82 (1960).
Derwent Farmdoc CPI No. 04589x/03 (1/22/74).

*Primary Examiner*—Gerald A. Schwartz
*Attorney, Agent, or Firm*—Robert A. Armitage

[57] ABSTRACT

This invention comprises certain analogs of the prostaglandins in which the C-1 carboxyl is replaced by a primary alcohol. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive cycle regulation, gastric antisecretory action, and the like.

2 Claims, No Drawings

2-DECARBOXY-2-HYDROXYMETHYL)-16-FLUORO-PGE$_2$ COMPOUNDS

The present application is a divisional application of Ser. No. 647,369 filed Jan. 8, 1976, now issued as U.S. Pat. No. 4,032,576 on June 28, 1977.

The present invention relates to prostaglandin analogs, for which the essential material constituting disclosure therefor is incorporated by reference here from Ser. No. 647,369, filed Jan. 8, 1976, now pending issuance as a United States Patent.

I claim:

1. A prostaglandin analog of the formula

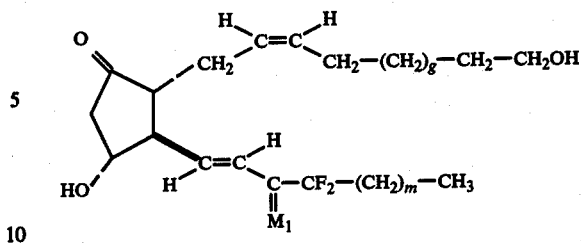

wherein M$_1$ is

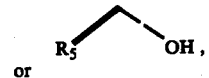

wherein
R$_5$ is hydrogen or methyl;
wherein g is one, 2, or 3; and
wherein m is one to 5, inclusive.

2. 2-Decarboxy-2-hydroxymethyl-16,16-difluoro-PGE$_2$.

* * * * *